(12) United States Patent
Kamkar

(10) Patent No.: US 9,681,805 B2
(45) Date of Patent: Jun. 20, 2017

(54) AFFERENT PUPIL TESTER

(71) Applicant: Babak Kamkar, Irvine, CA (US)

(72) Inventor: Babak Kamkar, Irvine, CA (US)

(*) Notice: Subject to any disclaimer, the term of this patent is extended or adjusted under 35 U.S.C. 154(b) by 361 days.

(21) Appl. No.: 13/935,470

(22) Filed: Jul. 3, 2013

(65) Prior Publication Data
US 2015/0223682 A1 Aug. 13, 2015

Related U.S. Application Data

(60) Provisional application No. 61/796,163, filed on Nov. 5, 2012.

(51) Int. Cl.
*A61B 3/11* (2006.01)
*A61B 3/00* (2006.01)

(52) U.S. Cl.
CPC ............ *A61B 3/112* (2013.01); *A61B 3/0008* (2013.01)

(58) Field of Classification Search
CPC .. A61B 3/14; A61B 3/12; A61B 3/103; A61B 3/02

USPC .......................... 351/200, 203, 205, 206, 246
See application file for complete search history.

(56) References Cited

U.S. PATENT DOCUMENTS

| | | | |
|---|---|---|---|
| 1,358,721 A | 11/1920 | Fujii | |
| 2,189,285 A | 2/1940 | Gruber | |
| 4,850,691 A | 7/1989 | Gardner | |
| 6,382,792 B1* | 5/2002 | Khoury | 351/205 |
| 6,474,815 B1* | 11/2002 | Ulbers et al. | 351/214 |
| 7,967,442 B2* | 6/2011 | Siminou | 351/246 |
| 2006/0268231 A1* | 11/2006 | Gil et al. | 351/221 |
| 2009/0109402 A1* | 4/2009 | Suba | 351/221 |
| 2009/0153797 A1* | 6/2009 | Allon et al. | 351/206 |
| 2012/0008091 A1* | 1/2012 | Stewart | 351/206 |
| 2012/0100136 A1* | 4/2012 | Patel et al. | 424/133.1 |

* cited by examiner

*Primary Examiner* — James Greece

(57) ABSTRACT

A new device, called Afferent Pupil Tester, designed for close up and magnified examination of both pupils at the same time, superimposed, as they react to direct and consensual light, comprises of high plus lenses, measuring grid, bright LED lights controlled with momentary switches, UV lights controlled by momentary switches, batteries, built-in camera and/or external camera, detachable facemask, and a sturdy casing.

19 Claims, 11 Drawing Sheets

Photos of an Example of a Prototype

AFFERENT PUPIL TESTER

CROSS-REFERENCE TO RELATED APPLICATIONS

This application claims the benefit of U.S. Provisional Application No. 61/796,163 filed Nov. 5, 2012, the disclosure of which is incorporated herein by reference.

BACKGROUND OF THE INVENTION

The embodiments described herein generally relate to a device for examining both pupils simultaneously and/or sequentially under high magnification, as well as examining and photo documenting the ocular surface and surrounding tissues under bright and blue/UV light under high magnification, using a simple-to-operate and portable ophthalmic device. More specifically, the embodiments relate to an improved technique for detecting afferent pupillary defect, and evaluating eyelids, conjunctiva, and corneal surface without a slit lamp biomicroscope.

Present day examination of the pupil in a clinical setting consists of shining a penlight in a patient's eye, and attempting to observe the ensuing pupillary constriction. The examiner must also peek into the contralateral eye to see if that pupil also reacts to the light, without having a direct light shined into it. This is called pupillary reaction to consensual light. In normal subjects, both pupils react equally to direct and consensual light. The next step is to swing the penlight back and forth between the two eyes while looking for continuous constriction. If one pupil begins to dilate, the integrity of the optic nerve in that eye comes under question. This is called the Swinging Flashlight Test and a positive or negative finding indicates the presence or absence of an afferent pupillary defect, or a Marcus Gunn Pupil. Some conditions that affect the optic nerve, thereby creating a positive afferent pupillary defect, include optic atrophy, glaucoma, and brain tumors.

Existing ophthalmic devices do not allow simultaneous view of both pupils in a superimposed image using the examiner's both eyes. Typically, the examiner uses one or both of his or her eyes to view only one anatomy part, such as one pupil, of the subject. There are no ophthalmic devices that allow the examiner to utilize both eyes at the same time to view each pupil of the subject.

SUMMARY OF THE INVENTION

An ophthalmic device according to one embodiment provides for a magnified view of both pupils while allowing the examiner to quickly shine a light in either pupil. The ophthalmic device called Afferent Pupil Tester is a portable hand-held device that includes a sturdy casing (e.g., from plastic) containing high plus lenses and fixed LED and blue/UV lights with easy controls for shining the light directly into each eye while being able to observe the pupil reaction under high magnification. A positive afferent pupillary defect in diseased, post-traumatic, or post-surgical eyes, in the presence of dark irises or small pupils can be better detected.

Therefore, the ophthalmic device according to one embodiment overcomes the difficulties associated with examination of pupils, especially in subjects with small or dark pupils or pupils that react sluggishly to direct or consensual light. Careful assessment of pupillary response is a valuable guide in differential diagnosis of many ocular and neurological conditions.

The ophthalmic device according to another embodiment allows the examiner to view both pupils under high magnification in real time simultaneously and superimposed, while being able to shine a harmless bright light on each pupil or both at will. With a similar technique to the penlight testing, reaction of each pupil to direct light is observed. Then the reaction of each pupil to light shined in the other eye is observed. This is called reaction to consensual light. Next the examiner sequentially shines the bright light to each eye while looking for a small detectable dilation of either pupil. If both pupils remain constricted or exhibit a small amount of further constriction followed by a small amount of dilation, called hippus, there is a negative afferent pupillary defect. This means the optic nerves transmit the light signal to the brain in an equal fashion and the pupils constrict to the same level. If one pupil starts to dilate when the lights are switched back and forth between the eyes, this indicates a positive afferent pupillary defect (APD). The usual cause of a positive APD is a loss of innervations in the optic nerve of the eye which exhibits the relative momentary pupillary dilation. The simultaneous and superimposed view of both pupils allows for easy comparison of pupil reaction.

The ophthalmic device according to other embodiments allows for quick and magnified examination of the anterior segments of the eye and its surrounding tissue, called the adnexa. The device provides a magnified view of the cornea. The device allows measurement of pupil diameters under various lighting conditions. The device is equipped with blue/UV LED lights that produce fluorescence with the additional instillation of fluorescein dye into the eye. The blue/UV LED lights in this device and fluorescein dye are also helpful in assessing fluorescein pattern of rigid cornea and scleral lenses. The portability and ease of use this device makes examination of the eyelids, conjunctiva, and cornea readily available to urgent care clinics as well as eye care providers. The device allows for digital photography or video recording of pupils, ocular surfaces, and surrounding areas using hand-held digital cameras, mobile phones, or optional built-in cameras.

Eye care providers can also view fluorescein pattern of certain rigid or hybrid contact lenses with the built-in blue/UV lights. The device contains a measuring grid which enables eye care providers to measure pupil sizes in various lighting conditions, from dim to bright.

The military would benefit from having this device readily available for its units that may encounter eye injuries. This device is of value to the military because of its portability and its quick assessment of the ocular structures as well as the pupil. Correct assessment of the pupil reaction in evaluating combat casualties on the battlefield could mean the difference between life and death, especially when life-saving measures are taken in time as subtle constriction of the pupil is perceived by using this device.

There are additional benefits by using this device in veterinary clinics. Animals have similar ocular structure and function to humans. Differential diagnosis of ocular injuries or infections in animals can be a difficult task without magnified view of the ocular structures. Furthermore, afferent pupillary defect is more valuable when the clinician is forced to depend on objective testing with limited subjective information, as in a veterinary clinic.

In other aspects, methods of examining the eye and the pupil by having features and advantages corresponding to those discussed above are provided.

BRIEF DESCRIPTION OF THE DRAWINGS

Figure 1:
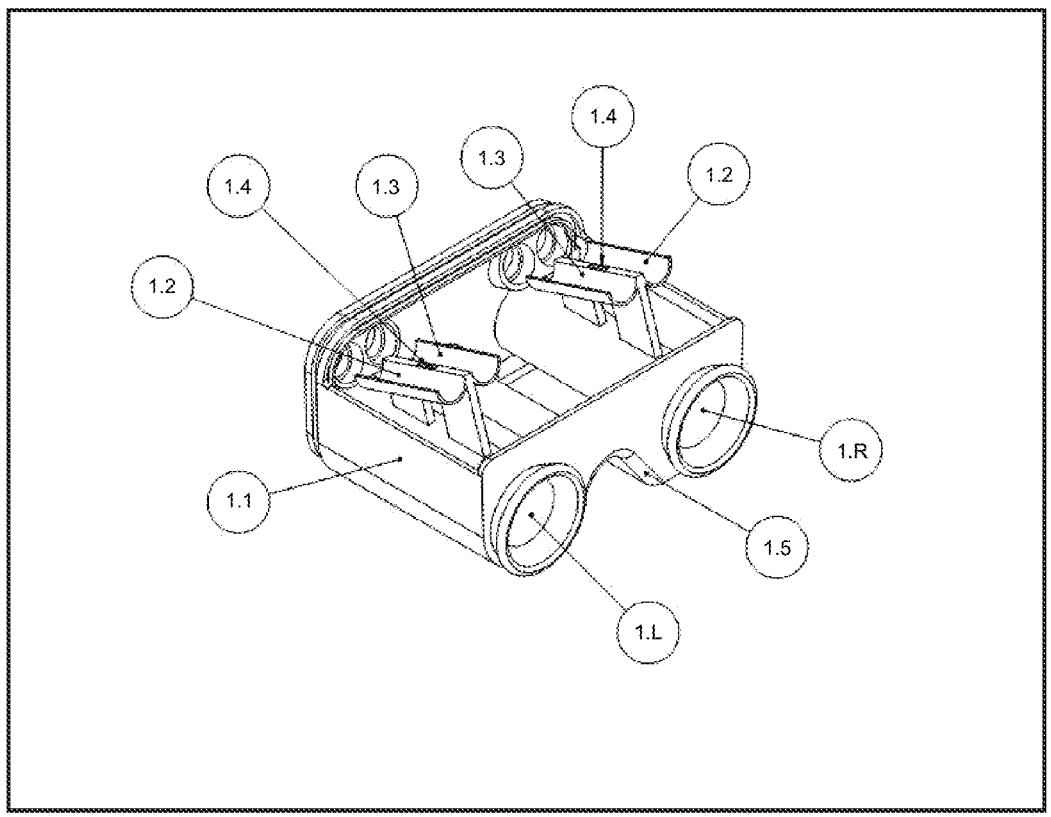

Having thus described various embodiments in general terms, reference will now be made to the accompanying drawings, which are not necessarily drawn to scale, and wherein:

FIG. 1 shows schematically an exemplary construction of an Afferent Pupil Tester, in accordance with one embodiment.

Figure 2:
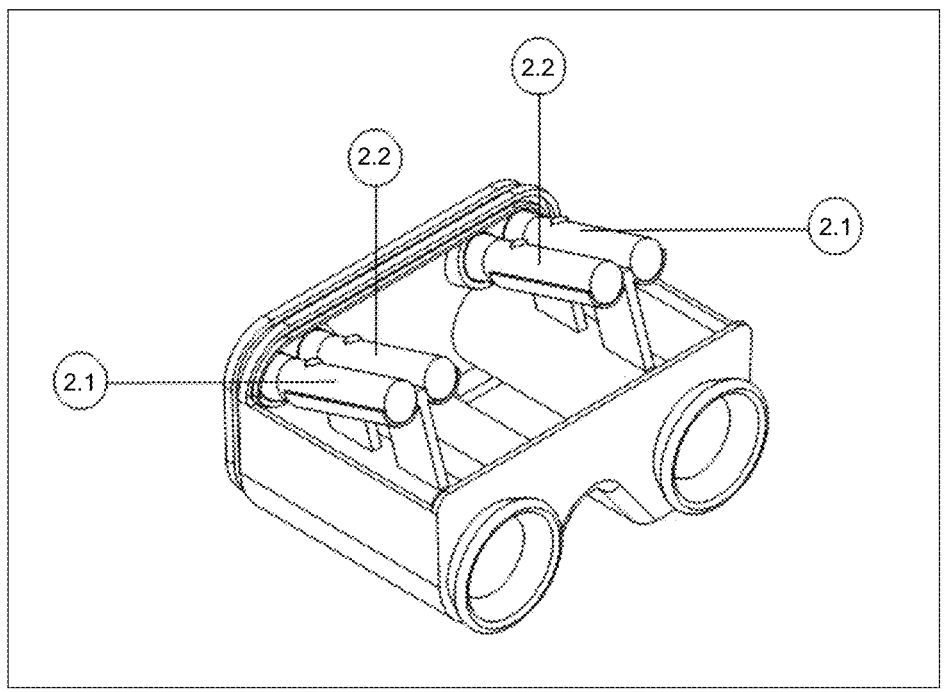

FIG. 2 shows the LED lights positioned inside their respective holders as shown in FIG. 1.

Figure 3:
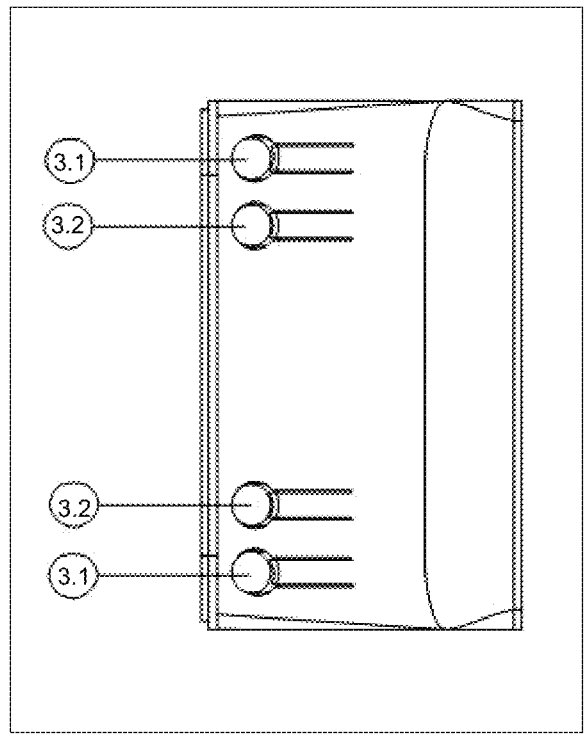

FIG. 3 shows the construction of the dome cover of the unit depicted in FIG. 2.

Figure 4:
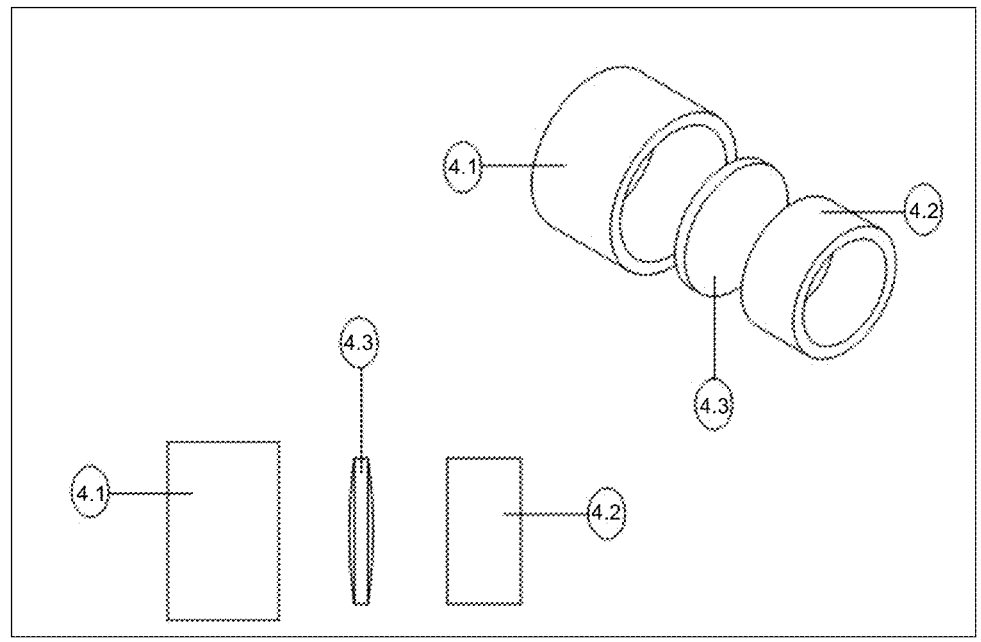

FIG. 4 shows the construction of lens holder for each lens tube.

Figure 5:
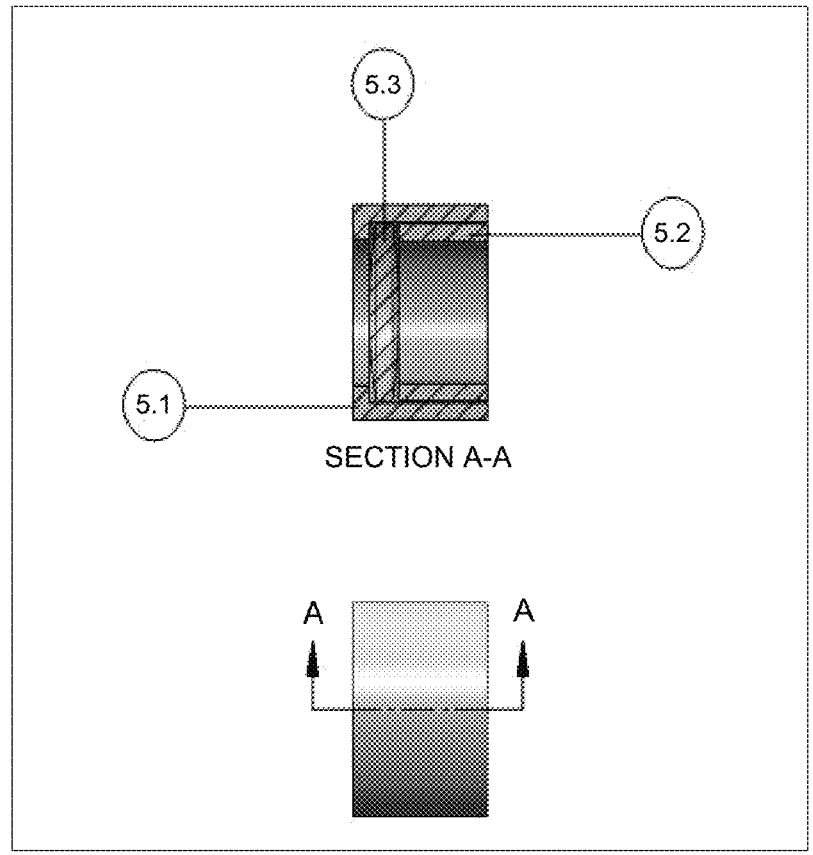

FIG. 5 shows the cross-section of the lens holder after assembly.

Figure 6:
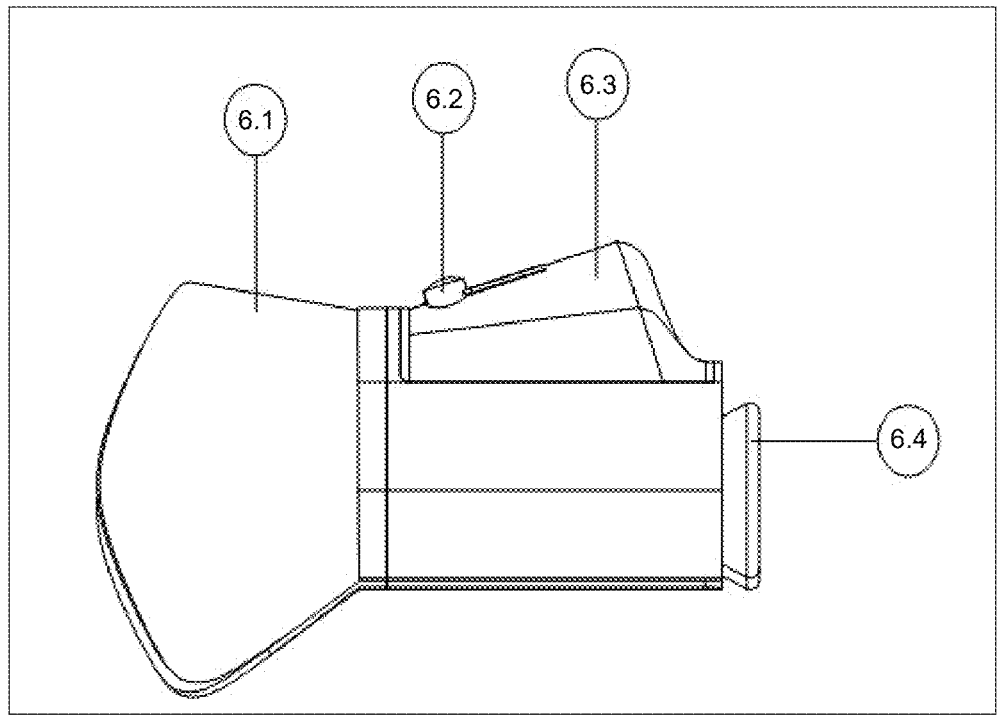

FIG. 6 shows the lateral view of the unit depicted in FIG. 2 with the dome cover in place and optional face mask attached.

Figure 7:
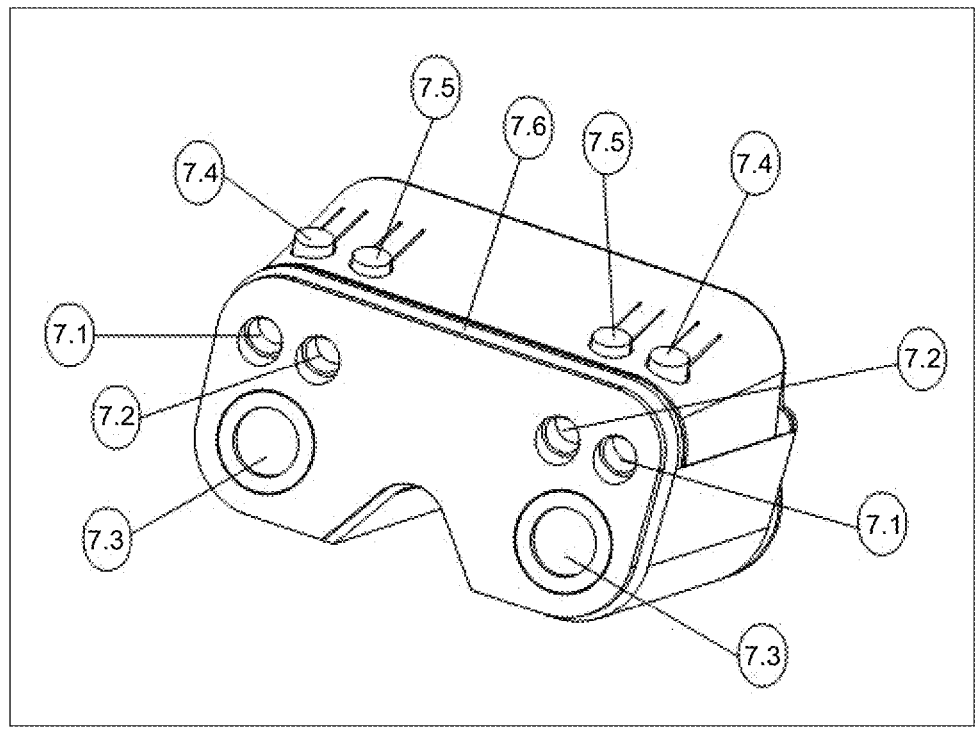

FIG. 7 shows frontal view (patient's view) of the unit depicted in FIG. 6 with the face mask removed.

Figure 8:
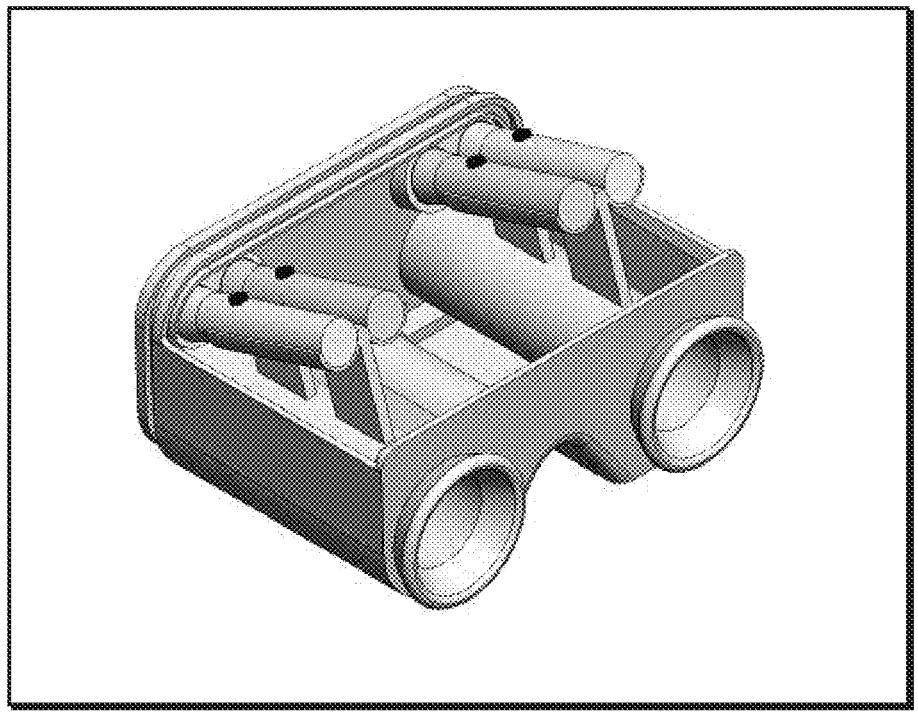

FIG. 8 shows three-dimensional graphic of an exemplary construction of the Afferent Pupil Tester with the LED lights positioned inside their respective holders.

Figure 9:
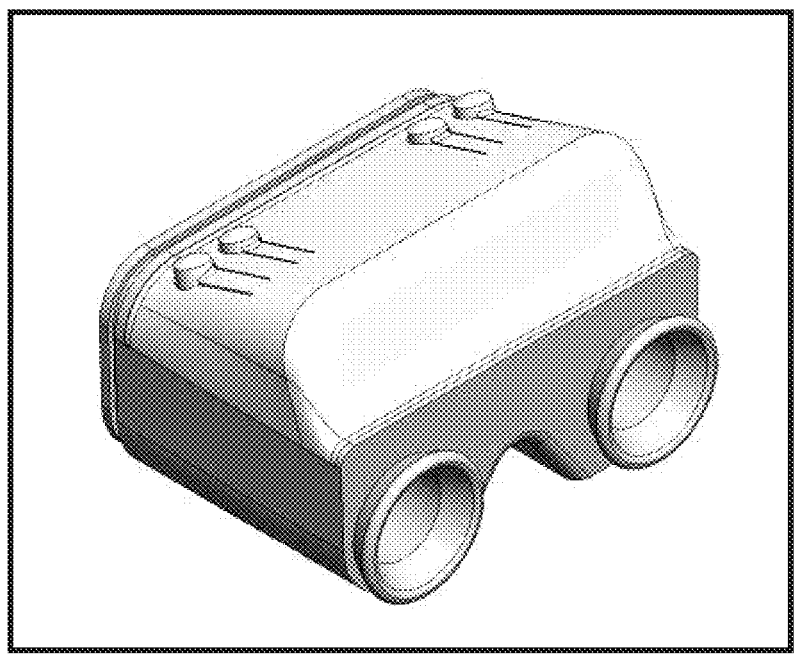

FIG. 9 shows the three-dimensional graphic of the unit depicted in FIG. 8 with the dome cover in place.

Figure 10:
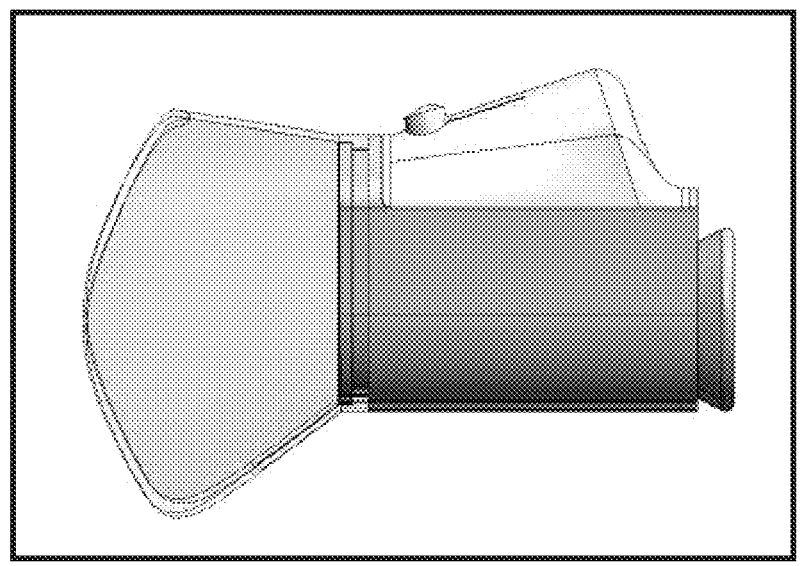

FIG. 10 shows the lateral three-dimensional graphic of the unit in FIG. 9 with the optional face mask attached.

Figure 11:
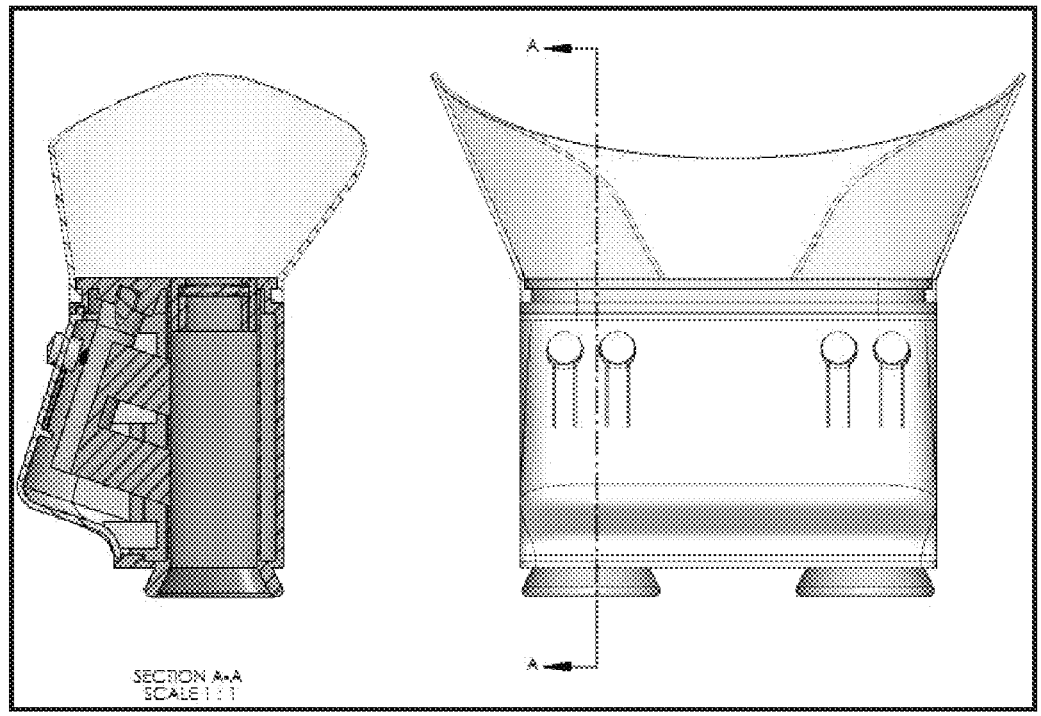

FIG. 11 shows the three-dimensional graphic and the cross-sectional view of the unit depicted in FIG. 10.

Figure 12:
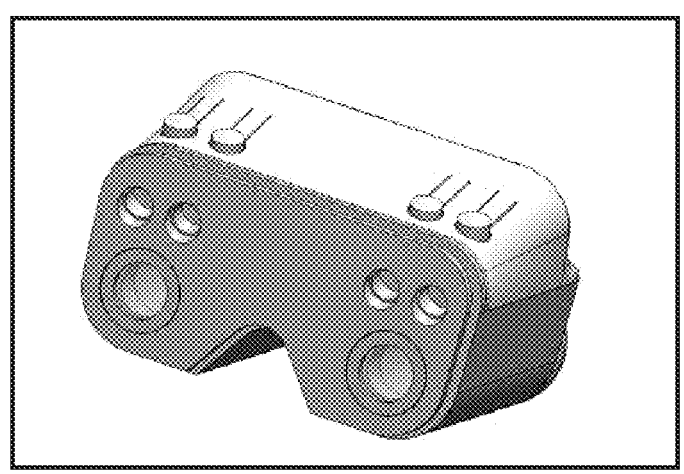

FIG. 12 shows the frontal or patient view of the unit depicted in FIG. 9 without the face mask.

Figure 13:
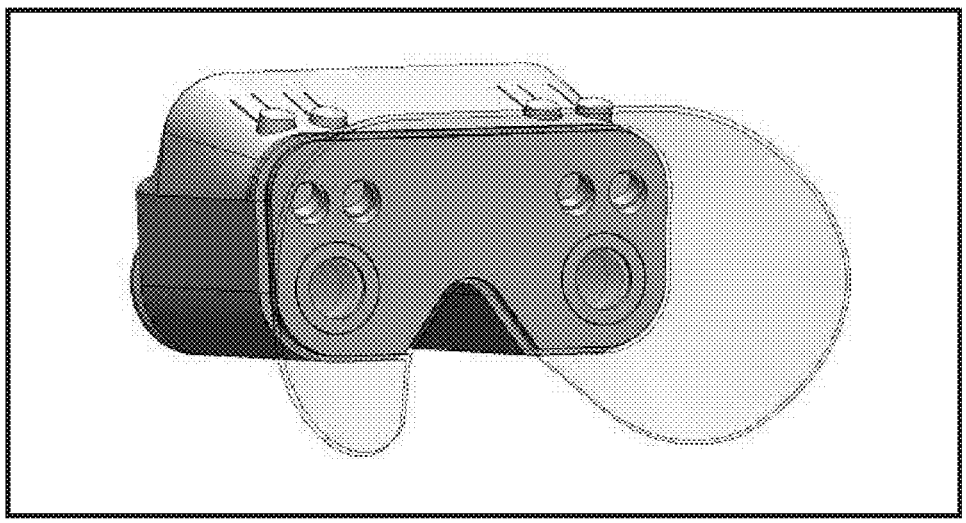

FIG. 13 shows the frontal or patient view of the unit depicted in FIG. 9 with the face mask attached.

Figure 14:

FIG. 14 shows the frontal view of an exemplary prototype of Afferent Pupil Tester.

Figure 15:
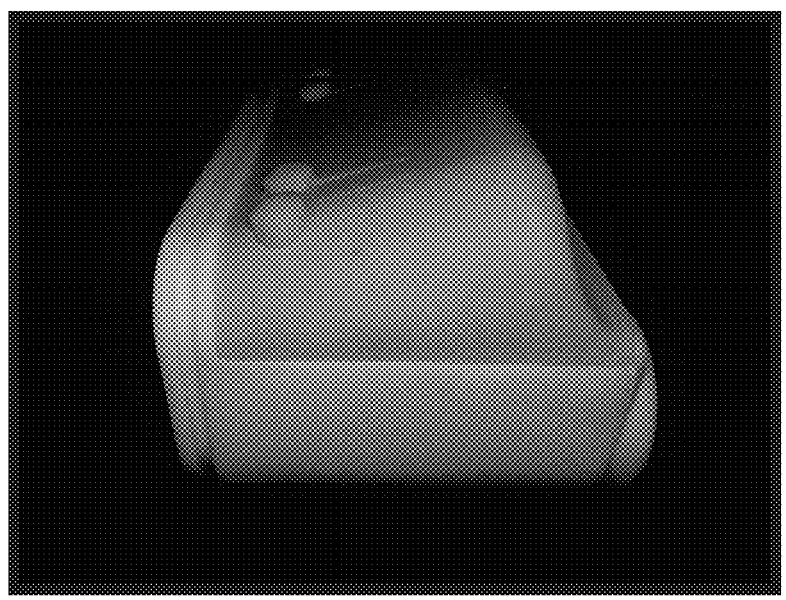

FIG. 15 shows the lateral view of the prototype shown in FIG. 14.

Figure 16:

FIG. 16 shows the observation tubes and oculars of the prototype in FIG. 14.

Figure 17:
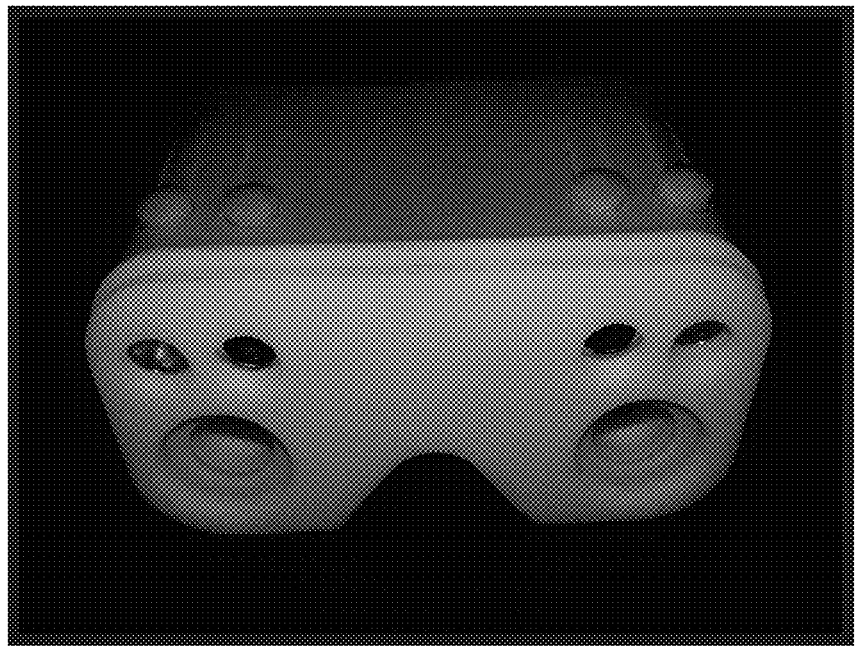

FIG. 17 shows the frontal (patient's) view of the prototype in FIG. 14.

Figure 18:
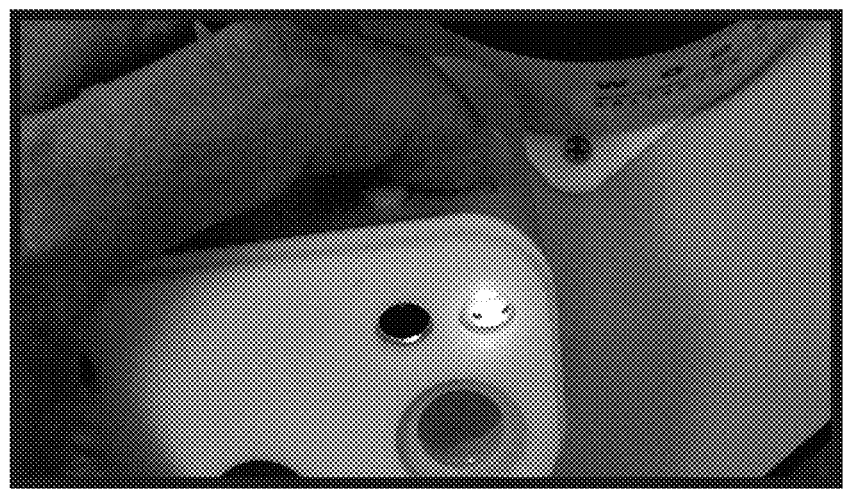

FIG. 18 shows the frontal view of the prototype in FIG. 14 with one UV LED light shining.

DETAILED DESCRIPTION OF THE INVENTION

The present invention now will be described more fully hereinafter with reference to the accompanying drawings. Indeed, the invention may be embodied in many different forms and should not be construed as limited to the embodiments set forth herein; rather, the embodiments are provided by way of example so that this disclosure will satisfy applicable legal requirements.

In accordance with embodiments described herein, the examiner's left eye views the right pupil of the subject, while examiner's right eye views the left eye of the subject at the same time in a superimposed image. When one light is shined, only the pupil that is being illuminated is perceived by the examiner, and when the light is quickly altered, the other eye is perceived immediately without any lapse in time. This method of examination allows for quick comparison of pupil reaction to a bright light and an improved detection of afferent pupillary defect. Additionally, the examiner has the option of closing one of his or her own eyes while concentrating on measurement of the pupil size or reaction in just one eye of the subject, in the direct or consensual method. The pupil examination of a darker iris is challenging. Additional factors such as small pupils, old age, underlying systemic conditions, such as diabetes, and history of trauma or ocular surgery can often cause a pupil to react slowly. Magnified view of both pupils while being able to quickly shine a light in either pupil can enhance the examination accuracy significantly.

FIG. 1 illustrates schematically an exemplary construction of the Afferent Pupil Tester, according to one embodiment. The reference number 1.1 points to the casing made of a sturdy material, such as plastic. The reference numbers 1.2 point to the plastic holdings for blue/ultra-violet LED lights angled in a manner to shine the light in the direction of the patient's corresponding eye. The reference numbers 1.3 point to the plastic holdings for white LED lights angled in a manner to shine the light in the direction of the patient's corresponding eye. The reference numbers 1.4 point to the slots in the plastic material used to slide tie wraps through to hold the LED lights in place. The reference number 1.5 points to the plastic curved area of the casing that is designed to rest over for the bridge of the nose of the examiner. The reference number 1.R points to the observation tube for the examiner's right eye, corresponding to the patient's left eye. The reference number 1.L points to the observation tube for the examiner's left eye, corresponding to the patient's right eye. The observation tubes may contain a clear lens an eyepiece, a half mirror to direct the light to a built-in camera as an optional feature of Afferent Pupil Tester, and an ocular high plus power lens, as described below in FIG. 4.

FIG. 2 shows the LED lights positioned inside their respective holders as shown in FIG. 1. The reference numbers 2.1 point to each blue/ultra-violet LED lights secured in the housing chamber with a tie wrap with the momentary switch facing directly upward. The reference numbers 2.2 point to each white LED lights secured in the housing chamber with a tie wrap with the momentary switch facing directly upward. The LED lights house their own long-lasting batteries, usually three Lithium coin cell batteries connected in sequence. The lifespan of these batteries with the expected use of this device in a typical clinic or ophthalmic office is several years. The batteries can easily be replaced by opening the end piece of each LED light.

FIG. 3 shows the removable dome cover of the Afferent Pupil Tester. The reference numbers 3.1 point to the levers that can be depressed by examiner triggering the momentary switches of the blue/ultraviolet LED lights that are housed directly under the dome cover. Likewise, reference numbers 3.2 point to the levers that can be depressed by examiner triggering the momentary switches of the white LED lights that are housed directly under the dome cover.

FIG. 4 shows one possible way to construct the lens holder and the ocular lens. The reference numbers 4.1 point to a hollow plastic tube slightly larger than high plus ocular lens so the lens would fit snuggly in the front of the tube against a rim. The reference numbers 4.2 point to the plastic hollow tube slightly smaller than the larger tube such that the smaller tube can be inserted inside the larger tube with a small force to overcome the friction of the two plastic hollow tubes. The reference numbers 4.3 point to the high plus ocular lens made from CR-39 material, polycarbonate, high-index lens, or glass. The ocular lens is placed in the larger tube and pushed forward to the rim in front of the larger tube, while the smaller tube is inserted following the lens and thereby holding the lens in place near the front of the large tube.

FIG. 5 shows the cross-sectional view of the lens holders and the ocular lens described in FIG. 4 as one assembled unit. The reference number 5.1 points to the outer larger tube with the rim holding the lens. The reference number 5.2 points to the inner smaller tube securing the lens posteriorly. The reference number 5.3 points to the high plus ocular lens held in place by the smaller tube. The high plus ocular lens may be of +20 to +25 diopters range. The ocular lenses may have a precise measuring grid printed on their surface with hash marks corresponding to 0.1 millimeter. The grid may be on a horizontal line measuring 15 millimeters across.

FIG. 6 shows a lateral or side view of Afferent Pupil Tester with the optional facemask attached. The reference number 6.1 points to a clear plastic or rubberized plastic mask that can snap to the front of the unit and would serve as a stabilizer against the patient's face. Transparent material is used in construction of the flexible mask to allow ambient light for pupil examination in dim to bright conditions. In between examinations, the mask can be safely wiped clean with commercially available rubbing alcohol packets and let air dry prior to subsequent use. The reference number 6.2 points to the lever control for the left blue/ultra-violet LED light. The reference number 6.3 points to the removable dome cover. The reference number 6.4 points to the eyepiece of the left observation tube.

FIG. 7 shows the frontal or patient view of Afferent Pupil Tester with the optional facemask detached. The reference numbers 7.1 point to the blue/ultra-violet LED lights. The reference numbers 7.2 point to the white LED lights. The reference numbers 7.3 point to the ocular lenses used to examine the corresponding patient's eyes. The reference numbers 7.4 point to the push-lever used to control the blue/ultra-violet LED light. The reference numbers 7.5 point to the push-lever used to control the white LED light. The reference number 7.6 points to the grooved rim area extending around the front of Afferent Pupil Tester used for the attachment of the rubberized facemask.

Three-dimensional graphics of Afferent Pupil Tester are included. FIG. 8 shows three-dimensional graphic of an exemplary construction of the Afferent Pupil Tester with the LED lights positioned inside their respective holders.

FIG. 9 shows the three-dimensional graphic of the unit depicted in FIG. 8 with the dome cover in place.

FIG. 10 shows the lateral three-dimensional graphic of the unit in FIG. 9 with the optional face mask attached.

FIG. 11 shows the three-dimensional graphic and the cross-sectional view of the unit depicted in FIG. 10.

FIG. 12 shows the frontal or patient view of the unit depicted in FIG. 9 without the face mask.

FIG. 13 shows the frontal or patient view of the unit depicted in FIG. 9 with the face mask attached.

Photos of a prototype are provided in FIGS. 14-18 as an example of the device.

FIG. 14 shows the frontal view of an exemplary prototype of Afferent Pupil Tester.

FIG. 15 shows the lateral view of the prototype shown in FIG. 14.

FIG. 16 shows the observation tubes and oculars of the prototype in FIG. 14.

FIG. 17 shows the frontal (patient's) view of the prototype in FIG. 14.

FIG. 18 shows the frontal view of the prototype in FIG. 14 with one UV LED light shining.

In one variation of the FIG. 1 embodiment, a half mirror angled at 45 degrees is placed in one or both observation tubes, such that the reflected light is directed toward the interior of the unit. An opening within the construction of the observation tube(s), corresponding to the reflected light(s), allows the entry of the reflected light into the interior chamber of the device. A micro camera (or two micro cameras) capable of recording still photographs or video is (are) situated within the chamber to capture the reflected light. The camera(s) is (are) connected to a battery compartment which can be accessed from under the device for replacement. The cameras record the images on an SD card which is also accessed from outside of the unit. In an alternative method, the camera(s) have Bluetooth capability to transfer the images to an external computer for review and storage. Alternative methods of image file transfer, such as a wired connection, is included in this description. The half mirror(s) allow the direct view of the ocular structures to the examiner without significant loss of image quality partially due to high intensity of LED lights and partially due to high quality of the half mirrors.

In yet another variation of the FIG. 1 embodiment, the observation tubes are constructed in such way that the distance between the eyepieces for the examiner (FIG. 1 pointer 1.R and 1.L) can be adjusted to match the examiner's pupillary distance, or PD (i.e., distance between pupils). Similarly the PD of the patient would be used to adjust the oculars facing the patient (FIG. 7, pointer 7.3).

While the present invention has been particularly shown and described with reference to exemplary embodiments thereof, it will be understood by one of ordinary skill in the art that various changes in form and details may be made therein without departing from the spirit and scope of the present invention as defined by the following claims. Therefore, the above description should not be taken as limiting the scope of the invention, which is defined by the appended claims.

What is claimed is:

1. A handheld device, comprising:
two observation tubes; and
two harmless bright lights angled in a manner to shine light in the direction of a subject's eyes during examination, wherein the two observation tubes contain plus lenses through which an examiner can directly look at and examine both pupils of a subject at close range and at the same time, superimposed, with the two harmless bright lights that cause pupils to react to direct and consensual light,
wherein the two harmless bright lights are adapted to enable the examiner to sequentially shine light between the two eyes causing each pupil to stay constricted in normal subjects.

2. The device according to claim 1, wherein sequential shining of the light between the two eyes can cause one pupil to dilate slowly thereby identifying compromised optic nerves, as in an afferent pupillary defect, or a Marcus Gunn Pupil.

3. The device according to claim 1, wherein integrated blue/UV light could be used to view superficial corneal defects in an eye where a fluorescein dye has been instilled, aiding in differential diagnosis of various red eye conditions, including injuries.

4. The device according to claim 1, wherein diameter of pupil in low dim light as well as in bright light can be measured.

5. The device according to claim 1, wherein fluorescein pattern of a rigid gas permeable lens, a hybrid lens, or a scleral lens can be evaluated with integrated blue/UV light.

6. The device according to claim 1, wherein an examiner can take photos or videos of the pupils, adnexa, cornea, and anterior segment by using a built-in camera or a hand-held camera, such as a mobile phone.

7. The device according to claim 1, wherein magnified photos or video of the eye or skin can be transmitted wirelessly to a nearby receiver such as a Bluetooth enabled computer or electronic device for analysis and storage.

8. A handheld pupil tester, comprising:
   two observation tubes through which an examiner can directly look at and examine both pupils of a subject at close range and at the same time, superimposed;
   holdings for holding lights angled in a manner to shine light in the direction of the subject's eye during examination; and
   one or more external levers that can be manipulated by the examiner to control the lights so as to enable the examiner to sequentially shine light between the two eyes.

9. The handheld pupil tester of claim 8 further comprising one or more batteries for powering the lights.

10. The handheld pupil tester of claim 8 wherein the lights further include white LED lights.

11. The handheld pupil tester of claim 8 wherein the lights include blue/ultra-violet LED lights.

12. The handheld pupil tester of claim 8 wherein the lights have one or more momentary switches coupled to the one or more external levers.

13. The handheld pupil tester of claim 8 further adapted to receive a facemask configured to serve as a stabilizer against the subject's face during examination.

14. The handheld pupil tester of claim 8 wherein each observation tube includes an eyepiece.

15. The handheld pupil tester of claim 8 further comprising a built-in camera configured to enable an examiner to take photos or videos of the pupils, adnexa, cornea, and anterior segment.

16. The handheld pupil tester of claim 15 wherein each observation tube includes a half mirror for directing light to the built-in camera.

17. The handheld pupil tester of claim 15 further configured to wirelessly transmit captured photos or video to an external electronic device.

18. A handheld pupil tester, comprising:
   a casing comprising:
      two observation tubes through which the examiner can directly look at and examine both pupils of a subject at close range and at the same time, superimposed;
      holdings for holding battery-powered LED lights angled in a manner to shine light in the direction of the subject's eye during examination; and
      a removable dome cover configured to be attach to the casing to encase the observation tubes and the LED lights, the removable dome cover having external levers that can be manipulated by an examiner to control the LED lights so as to enable the examiner to sequentially shine light between the two eyes.

19. The handheld pupil tester of claim 18 further comprising a built-in camera configured to enable an examiner to take photos or videos of a subject's eyes and wirelessly transmit captured photos or videos to an electronic device.

* * * * *